United States Patent
Burkholz

(10) Patent No.: US 9,839,385 B2
(45) Date of Patent: Dec. 12, 2017

(54) INTEGRATED CLOSED IV LINE DRAW SYSTEM

(71) Applicant: Becton, Dickinson and Company, Franklin Lakes, NJ (US)

(72) Inventor: Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 614 days.

(21) Appl. No.: 13/927,583

(22) Filed: Jun. 26, 2013

(65) Prior Publication Data

US 2015/0005669 A1    Jan. 1, 2015

(51) Int. Cl.
| | |
|---|---|
| *A61B 5/15* | (2006.01) |
| *A61B 5/153* | (2006.01) |
| *A61B 5/154* | (2006.01) |
| *A61B 5/155* | (2006.01) |

(52) U.S. Cl.
CPC .... *A61B 5/150992* (2013.01); *A61B 5/15003* (2013.01); *A61B 5/153* (2013.01); *A61B 5/150236* (2013.01); *A61B 5/150244* (2013.01); *A61B 5/150343* (2013.01); *A61B 5/150503* (2013.01); *A61B 5/150732* (2013.01); *A61B 5/154* (2013.01); *A61B 5/155* (2013.01); *A61B 5/15074* (2013.01); *A61B 5/150389* (2013.01); *A61B 5/150572* (2013.01)

(58) Field of Classification Search
CPC . A61B 5/153; A61B 5/150992; A61B 5/1427; A61B 5/154; A61B 5/1438; A61B 5/155

USPC .................................................. 600/576, 577
See application file for complete search history.

(56) References Cited

U.S. PATENT DOCUMENTS

| | | | |
|---|---|---|---|
| 3,931,815 A | 1/1976 | Takatsuki | |
| 4,392,499 A * | 7/1983 | Towse | A61B 5/1438 600/577 |
| 5,084,034 A * | 1/1992 | Zanotti | A61B 5/15003 600/575 |
| 5,086,783 A | 2/1992 | Macors et al. | |
| 5,147,329 A | 9/1992 | Brannon | |
| 5,360,011 A * | 11/1994 | McCallister | A61B 5/1438 600/576 |
| 5,951,491 A * | 9/1999 | Wu | A61B 5/15003 600/576 |
| 6,155,991 A | 12/2000 | Beat et al. | |

(Continued)

FOREIGN PATENT DOCUMENTS

| | | |
|---|---|---|
| EP | 0 462 814 A1 | 12/1991 |
| EP | 1 366 711 A1 | 12/2003 |
| WO | 86/05683 | 10/1986 |

*Primary Examiner* — Max Hindenburg
*Assistant Examiner* — Jonathan M Foreman
(74) *Attorney, Agent, or Firm* — Jeanne Lukasavage; Craig Metcalf; Kirton McConkie

(57) ABSTRACT

The present invention extends to a closed IV line draw system which may be used with a PIVC or another vascular access device to collect blood samples. The closed IV line draw system consists of various integrated components that allow the system to remain closed during the blood collection process. In this way, the closed IV line draw system simplifies the blood collection process and reduces the risk of contamination to the PIVC or other vascular access device.

4 Claims, 11 Drawing Sheets

(56) References Cited

U.S. PATENT DOCUMENTS 6,355,023 B1* 3/2002 Roth .................... A61B 5/1438
            604/411
2005/0267384 A1 12/2005 Sauer et al.

* cited by examiner

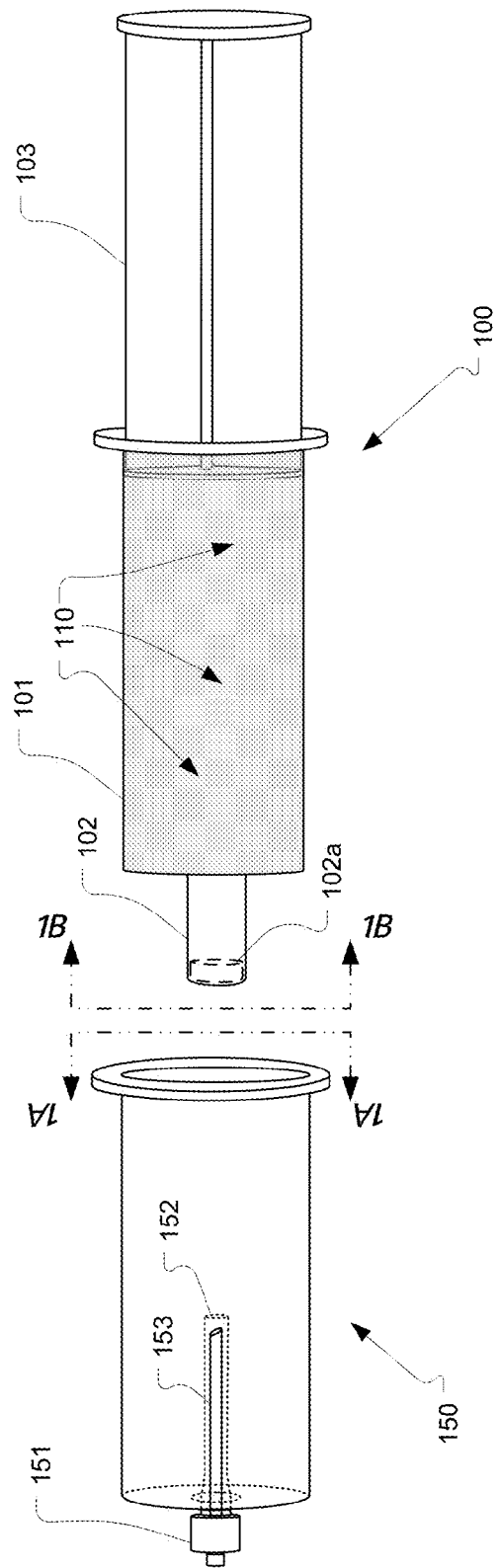

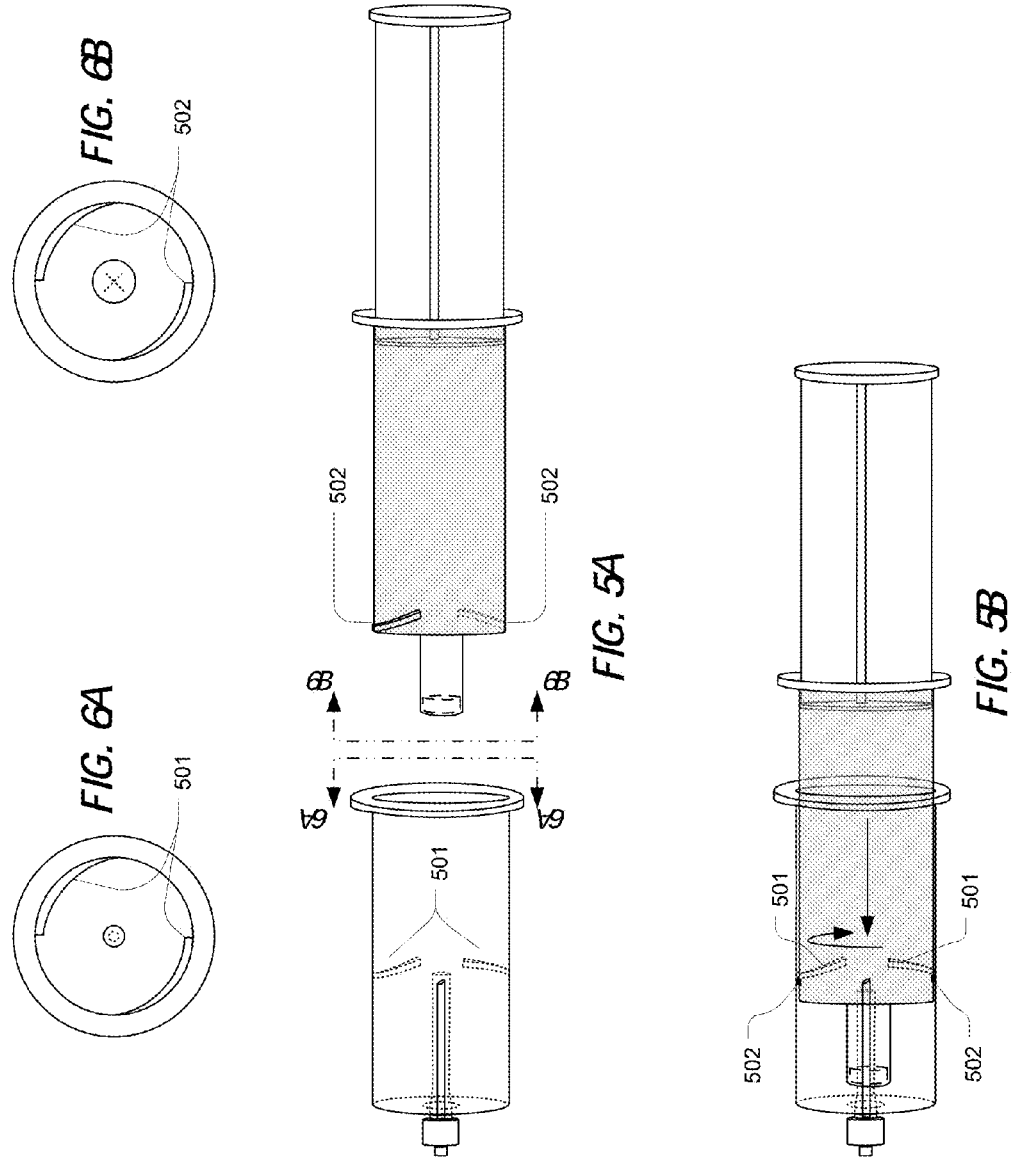

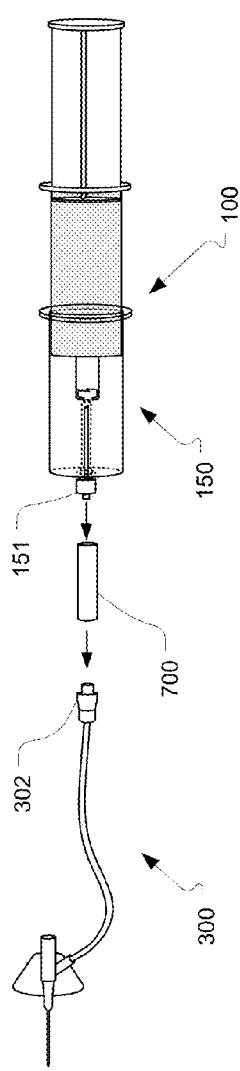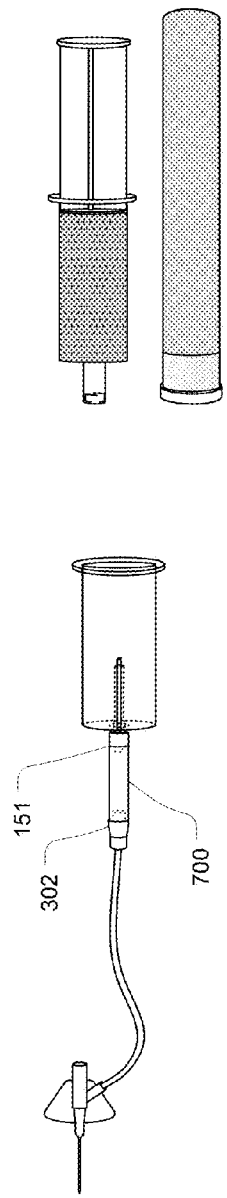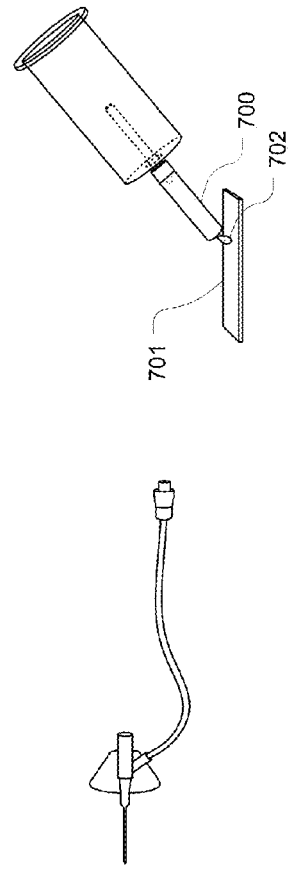

INTEGRATED CLOSED IV LINE DRAW SYSTEM

BACKGROUND OF THE INVENTION

The present invention relates generally to closed IV line draw systems for use with a peripheral intravascular catheter ("PIVC") or other vascular access device to collect blood.

A PIVC is a catheter that is used to provide access to a patient's vasculature. A PIVC is placed into a peripheral vein in order to administer medication or fluid, or to draw blood. The PIVC is introduced into the vein using a needle which is subsequently removed while the cannula of the PIVC remains in the vein to provide access. The catheter is then commonly taped to the patient's skin. PIVCs are generally believed to be the most commonly used means for vascular access in medicine.

An example of a PIVC is shown as element 300 in FIG. 3. As stated above, a PIVC is commonly used to draw blood from a patient such as when the patient has been admitted to a hospital. In typical usage, when a PIVC is used to draw blood from the patient, various different components and steps are required.

First, in order to ensure that the blood drawn through the PIVC represents an appropriate sample and does not contain contaminants, a syringe containing saline is attached to the PIVC (e.g. via connector 302 of the system 300 shown in FIG. 3) to flush the system. The saline is injected into the PIVC where it mixes with any fluids (including blood) or medications that may be present in the PIVC.

Second, a mixture of the saline and blood (known as a discard sample) is removed from the system. This step can be performed using a syringe or a vacuum sealed blood tube. The syringe or vacuum sealed blood tube sucks the discard sample from the PIVC so that only fresh blood remains within the PIVC.

Third, one or more blood draw samples are collected (e.g. using an access device and/or a vacuum sealed blood tube). For example, one or more vacuum sealed blood tubes are commonly attached to the PIVC. While attached, the vacuum present in the tubes causes blood to flow from the PIVC and into the tubes.

Fourth, in some cases, a small blood sample for point-of-care ("POC") testing is collected. POC testing refers to tests that are performed at or near the site of patient care. For example, the technician that obtains the POC sample can test the sample within the room in which the patient is located. POC testing allows many tests to be performed immediately to thereby provide quick results to the patient or health care professional. POC testing is often used to provide blood glucose readings, blood gas and electrolyte analysis, rapid coagulation testing, drug abuse screenings, and other tests where immediate results are desirable.

With each of these steps, a different device may be connected to and disconnected from the PIVC. For example, in typical approaches, three connections to/disconnections from the PIVC are made during the blood collection process. Attaching and removing these devices to the PIVC can make the blood collection process cumbersome. For example, to perform a blood draw in such cases, the technician must be provided with the multiple devices, must unwrap and connect each device, and then disconnect and dispose of each device. Also, each time the technician connects or disconnects a device from the PIVC, there is an increased possibility that the technician will be exposed to the patient's blood (e.g. via needle sticks). Additionally, each time a device is removed from the PIVC, the PIVC becomes an opened system thereby increasing the possibility of contamination. Accordingly, current approaches for drawing blood using a PIVC require a substantial amount of time and create an enhanced risk for contamination.

BRIEF SUMMARY OF THE INVENTION

The present invention extends to a closed IV line draw system which may be used with a PIVC or another vascular access device to collect blood samples. The closed IV line draw system consists of various integrated components that allow the system to remain closed during the blood collection process. Because the components are integrated, the closed IV line draw system can be viewed initially as a singular component that requires only a single connection to the PIVC. Further, as the individual components of the closed IV line draw system are used, they can be independently removed from the remaining components of the closed IV line draw system thereby allowing the system to remain closed. In this way, the closed IV line draw system simplifies the blood collection process and reduces the risk of contamination to the PIVC or other vascular access device.

In some embodiments, the present invention is implemented as a closed IV line draw system that comprises an adapter for connecting the closed IV line draw system to a vascular access device, and a syringe integrated within the adapter. The syringe is configured to flush the vascular access device and collect a discard sample without being removed from the adapter and without disconnecting the adapter from the vascular access device.

In some embodiments, the syringe is configured to be removed from the adapter after the discard sample has been collected while the adapter remains connected to the vascular access device.

In some embodiments, the adapter comprises an open-ended shape into which the syringe is integrated, while the adapter includes a cannula that punctures a septum in the syringe when the syringe is advanced into the adapter.

In some embodiments, the syringe is initially integrated into the adapter such that the septum is positioned adjacent to a tip of the cannula prior to the adapter being connected to the vascular access device.

In some embodiments, after the discard sample is collected, the syringe is removed from the adapter thereby allowing a vacuum-sealed blood tube to be inserted over the cannula to collect blood from the vascular access device.

In some embodiments, closed IV line draw system can include a point-of-care dispensing adapter having a first and a second end where the first end is connected to the adapter and the second end is configured to attach to the vascular access device.

In some embodiments, the POC dispensing adapter retains an amount of blood that flows through the POC dispensing adapter and the adapter such that, when the closed IV line draw system is disconnected from the vascular access device, the amount of blood can be dispensed directly from the POC dispensing adapter.

In some embodiments, the amount of blood is dispensed from the POC dispensing adapter while the POC dispensing adapter remains connected to the adapter.

In some embodiments, the vascular access device is a PIVC, and the adapter comprises a locking luer connection for locking the adapter to the PIVC.

In some embodiments, the syringe is held within the adapter by an interface that requires the syringe to be rotated with respect to the adapter for the syringe to be removed from the adapter.

In some embodiments, the syringe can be removed from the adapter after flushing the vascular access device but without first collecting a blood sample. Similarly, in some embodiments, the syringe can initially supplied without a flushing fluid so that a blood sample can be collected without first flushing the vascular access device.

In other embodiments, the present invention is implemented as a closed IV line draw system comprising an adapter for connecting the closed IV line draw system to a vascular access device, the adapter including a cannula positioned in an interior of the adapter; and a syringe positioned within the adapter such that a tip of the syringe is positioned adjacent a tip of the cannula. The syringe is configured to be advanced into the adapter such that the tip of the syringe is punctured by the tip of the cannula thereby allowing for the flushing of the vascular access device and the collection of a discard sample without removing the syringe from within the adapter and without disconnecting the adapter from the vascular access device.

In some embodiments, the syringe is configured to be removed from the adapter after the discard sample has been collected while the adapter remains connected to the vascular access device.

In some embodiments, after the discard sample is collected, the syringe is removed from the adapter thereby allowing a vacuum-sealed blood tube to be inserted over the cannula to collect blood from the vascular access device.

In some embodiments, the closed IV line draw system includes a point-of-care dispensing adapter having a first and a second end where the first end is connected to the adapter, and the second end is configured to attach to the vascular access device.

In some embodiments, the POC dispensing adapter retains an amount of blood that flows through the POC dispensing adapter and the adapter such that, when the closed IV line draw system is disconnected from the vascular access device, the amount of blood can be dispensed directly from the POC dispensing adapter.

In some embodiments, the amount of blood is dispensed from the POC dispensing adapter while the POC dispensing adapter remains connected to the adapter.

In other embodiments, the present invention is implemented as a closed IV line draw system that comprises: a point-of-care dispensing adapter having a first and a second end, the second end being configured to attach to a vascular access device; an adapter connected to the first end of the POC dispensing adapter, the adapter comprising an open-ended container and having a cannula positioned within the interior of the container; and a syringe integrated within the interior of the adapter, the syringe being configured to flush the vascular access device and collect a discard sample without being removed from the adapter and without disconnecting the adapter from the vascular access device.

In some embodiments, the syringe is configured to be removed from the adapter after the discard sample has been collected while the adapter and POC dispensing adapter remain connected to the vascular access device.

In some embodiments, the POC dispensing adapter retains an amount of blood that flows through the POC dispensing adapter and the cannula of the adapter such that, when the closed IV line draw system is disconnected from the vascular access device, the amount of blood can be dispensed directly from the POC dispensing adapter while the POC dispensing adapter remains connected to the adapter.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1 illustrates an exploded side view of a closed IV line draw system that includes an adapter and a syringe;

FIG. 1A illustrates a top view of the adapter in FIG. 1 which is used to connect the closed IV line draw system to a vascular access device;

FIG. 1B illustrates a bottom view of the syringe of FIG. 1 which is integrated within the adapter of the closed IV line draw system;

FIG. 5A illustrates a securing mechanism that can be formed on the adapter and syringe to retain the syringe within the adapter while the plunger of the syringe is pulled outwardly;

FIG. 5B illustrates the adapter and plunger of FIG. 5A after the plunger has been secured within the adapter using the securing mechanism;

FIG. 6A illustrates a top view of the adapter of FIGS. 5A and 5B;

FIG. 6B illustrates a bottom view of the syringe of FIGS. 5A and 5B;

FIG. 7A illustrates that a POC dispensing adapter is connected between a connector of an adapter of a closed IV line draw system and a connector of a PIVC;

FIG. 7B illustrates that the POC dispensing adapter of FIG. 7A remains connected between the adapter and the PIVC while the discard sample and blood samples are extracted; and FIG. 7C illustrates that, once the blood collection process is completed, the POC dispensing adapter can be disconnected from the connector and an amount of blood that remains within the POC dispensing adapter can be dispensed on a POC tester for testing.

DETAILED DESCRIPTION OF THE INVENTION

Figure 2:
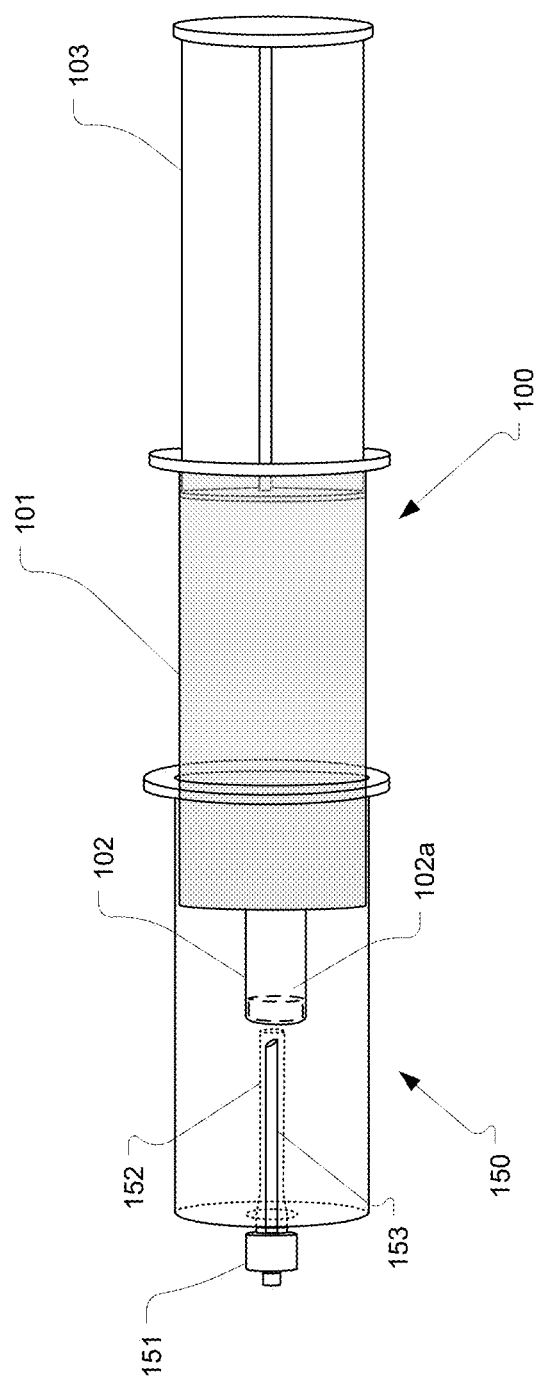
FIG. 2 illustrates a side view of the assembled closed IV line draw system of FIG. 1.

The present invention extends to a closed IV line draw system which may be used with a PIVC or another vascular access device to collect blood samples. The closed IV line draw system consists of various integrated components that allow the system to remain closed during the blood collection process. Because the components are integrated, the closed IV line draw system can be viewed initially as a singular component that requires only a single connection to the PIVC. Further, as the individual components of the closed IV line draw system are used, they can be independently removed from the remaining components of the closed IV line draw system thereby allowing the system to remain closed. In this way, the closed IV line draw system simplifies the blood collection process and reduces the risk of contamination to the PIVC or other vascular access device.

In some embodiments, the present invention is implemented as a closed IV line draw system that comprises an adapter for connecting the closed IV line draw system to a vascular access device, and a syringe integrated within the adapter. The syringe is configured to flush the vascular access device and collect a discard sample without being removed from the adapter and without disconnecting the adapter from the vascular access device.

In other embodiments, the present invention is implemented as a closed IV line draw system comprising an adapter for connecting the closed IV line draw system to a vascular access device, the adapter including a cannula positioned in an interior of the adapter; and a syringe positioned within the adapter such that a tip of the syringe is positioned adjacent a tip of the cannula. The syringe is configured to be advanced into the adapter such that the tip of the syringe is punctured by the tip of the cannula thereby allowing for the flushing of the vascular access device and the collection of a discard sample without removing the syringe from within the adapter and without disconnecting the adapter from the vascular access device.

In other embodiments, the present invention is implemented as a closed IV line draw system that comprises: a point-of-care dispensing adapter having a first and a second end, the second end being configured to attach to a vascular access device; an adapter connected to the first end of the POC dispensing adapter, the adapter comprising an open-ended container and having a cannula positioned within the interior of the container; and a syringe integrated within the interior of the adapter, the syringe being configured to flush the vascular access device and collect a discard sample without being removed from the adapter and without disconnecting the adapter from the vascular access device.

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

FIG. 1 illustrates an exploded view of a closed IV line draw system that includes an adapter 150 and a syringe 100. As shown, adapter 150 has an open-ended shape (e.g. a cylindrical shape) and includes a connector 151 on an exterior of adapter 150 and a cannula 153 positioned within the interior of adapter 150. Connector 151 can be any suitable type of connector and can be selected based on the type of catheter (e.g. a PIVC) to which it will be connected. Connector 151 and cannula 153 are structured to provide a channel through which fluids may flow. For example, connector 151 can include an interior passage that connects to an interior passage in cannula 153.

In some embodiments, it may be desirable to protect cannula 153 until the closed IV line draw system is to be used. In such cases, cannula 153 can be protected by a sheath 152 that covers the cannula until syringe 100 is forced overtop of cannula 153. Sheath 152 can be made of any suitable material that ruptures when syringe 100 is pressed against cannula 153 thereby allowing fluid to flow out through the channel in cannula 153.

Syringe 100 includes a body 101 that contains fluid 110 (e.g. saline), a tip 102 extending from body 101, and a plunger 103 for dispensing fluids from and collecting fluids into body 101. Tip 102 can be sealed by a septum 102a. Septum 102a can be made of any suitable material that can be punctured by cannula 153 to provide a fluid pathway between cannula 153 and syringe body 101.

FIG. 1A illustrates a top view of adapter 150 to illustrate the relative position of cannula 153 within the interior of adapter 150. As shown, cannula 153 can be positioned in the center of the adapter 150. However, in other embodiments, cannula 153 can be positioned in a location other than the center of adapter 150 (e.g. towards one side). In any case, the position of cannula 153 can be selected to correspond with the relative position of tip 102 of syringe 100.

FIG. 1B illustrates a bottom view of syringe 100. As shown in FIG. 1B, tip 102 is sealed with a septum 102a through which cannula 153 extends when syringe 100 is inserted into adapter 150, and which may reseal tip 102 after cannula 153 has been extracted. In some embodiments, septum 102a can include one or more perforations or slits to facilitate puncturing septum 102a with cannula 153. Septum 102a can also be configured, in some embodiments, to reseal after cannula 153 is removed from septum 102a.

FIG. 2 illustrates an assembled view of the closed IV line draw system of FIG. 1. As shown, syringe 100 is integrated within adapter 150. In this way, the closed IV line draw system initially functions as a singular component. Accordingly, a technician need only attach the singular closed IV line draw system to the PIVC or other catheter a single time. This facilitates not only the process of drawing blood, but also the preparation for drawing blood since a single integrated device is all the technician needs to obtain.

The closed IV line draw system can be initially supplied with syringe 100 already contained within adapter 150 (e.g. as shown in FIG. 2). Alternatively, the closed IV line draw system can be initially supplied with syringe 100 separated from adapter 150. In such cases, the technician can insert syringe 100 into adapter 150 to form the singular closed IV line draw system. In many cases when syringe 100 is supplied separated from adapter 150, it may be preferred to inset syringe 100 into adapter 150 prior to connecting adapter 150 to the PIVC or other catheter. However, the present invention can also be implemented by first connecting adapter 150 to the PIVC and then inserting syringe 100 into adapter 150.

Regardless of how the closed IV line draw system is initially supplied, once adapter 150 is connected to the PIVC or other catheter, adapter 150 need not be disconnected from the PIVC or other catheter until the blood draw process is complete as will be further described below with reference to FIGS. 4A-4E. In this way, the connection between the PIVC or other catheter and adapter 150 remains closed throughout the entire blood draw process.

When the closed IV line draw system is initially supplied with syringe 100 already contained within adapter 150, syringe 100 may be positioned so that tip 102 is adjacent to the tip of cannula 153. In this position, cannula 153 does not extend through septum 102a thereby preventing the fluid within syringe body 101 from escaping while the technician attaches adapter 150 to the PIVC. Further, because tip 102 is initially positioned close to cannula 153, only minimal movement of syringe 100 is required to activate syringe 100 for flushing the PIVC.

Figure 3:
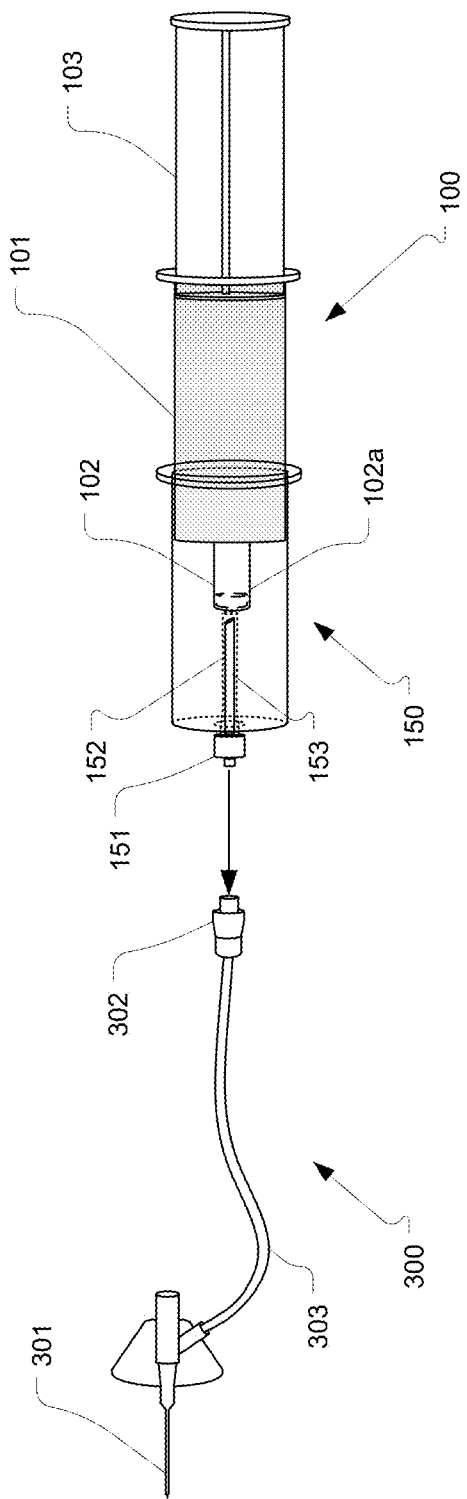
FIG. 3 illustrates the closed IV line draw system in conjunction with a PIVC.

FIG. 3 illustrates the closed IV line draw system of FIG. 2 in conjunction with a PIVC 300. As shown, PIVC 300 includes a needle 301 for inserting the PIVC within a patient's vasculature, a tube 303 through which fluids may flow from or into the patient's vasculature, and a connector 302 for connecting PIVC 300 to other devices. Connector 151 of the closed IV line draw system can be configured to attach to connector 302 of the PIVC. For example, connector 151 and connector 302 may employ luer connectors or another connector commonly used on intravenous access devices.

In a typical usage, needle 301 is inserted in the hand or wrist of a patient while tube 303 and/or connector 302 are secured to the patient using tape. PIVC 300 may be inserted into the patient at a prior time and remain inserted until the time at which the closed IV line draw system of the present invention is used.

Figure 4A:
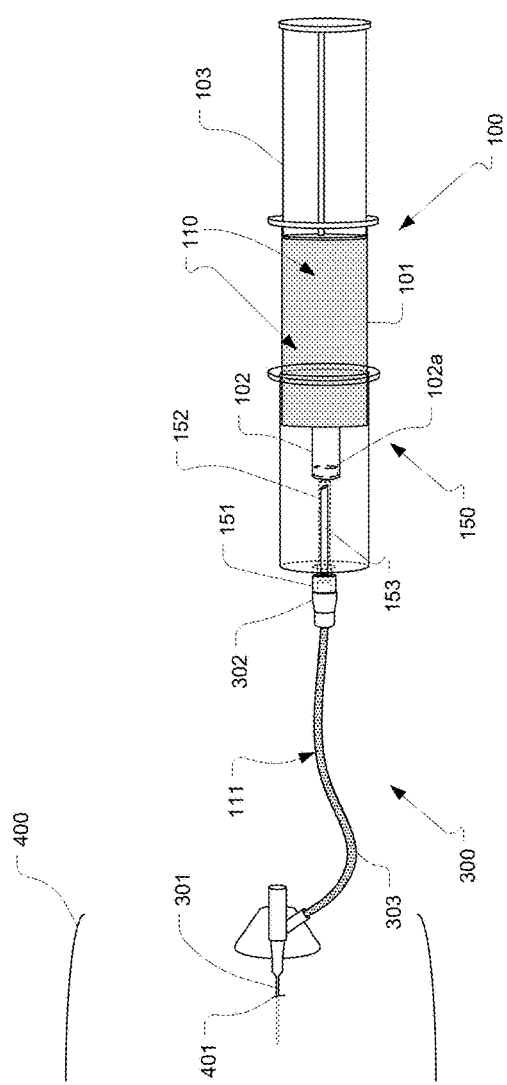
FIG. 4A illustrates that a needle of a PIVC, to which a closed IV line draw system has been attached, has been inserted into the vasculature of a patient.

FIGS. 4A-4F illustrate how the closed IV line draw system can be used during the blood draw process according to one or more embodiments of the invention. FIG. 4A illustrates that needle 301 of PIVC 300 has been inserted 401 into the vasculature of a patient 400. In this case, because a PIVC is used, needle 301 is inserted into a peripheral vein. However, the closed IV line draw system can equally be used when a different type of catheter is used such as when a central venous catheter or an arterial catheter is used. It is also feasible to use the closed IV line draw system with virtually any type of catheter.

With needle 301 inserted into the vasculature of patient 400, blood 111 can flow into tube 303 towards connector 302. Although not shown, typically a clamp would be provided on tube 303 to prevent blood from flowing through tube 303 when not desired. Connector 151 of adapter 150 has been connected to connector 302 of PIVC 300. Syringe 100 is also shown containing fluid 110 which may commonly be saline. The closed IV line draw system otherwise is in the same configuration as shown in FIG. 3. In other words, in FIG. 4A, syringe tip 102 is positioned adjacent to cannula 153 awaiting activation.

Figure 4B:
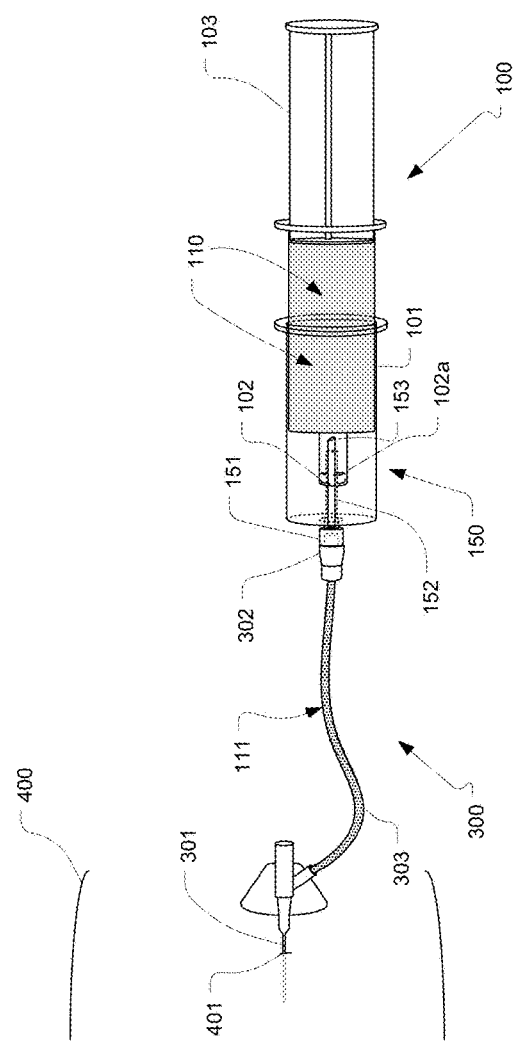
FIG. 4B illustrates that the syringe of the closed IV line draw system has been inserted further into the adapter such that the sheath has been retracted thereby exposing the cannula which pierces the tip of the syringe.

FIG. 4B illustrates that syringe 100 has been inserted further into adapter 150 such that sheath 152 has been retracted thereby exposing cannula 153 which pierces tip 102 (or septum 102a) of syringe 100. In this way, a fluid path is created from the body 101 to tube 303. As shown in FIGS. 5 and 6, syringe 100 can be held in this position using various securing mechanisms as further described below. Also, in embodiments where a sheath is not used, cannula 153 can slide directly through septum 102a without requiring the rupturing of sheath 152.

Figure 4C:
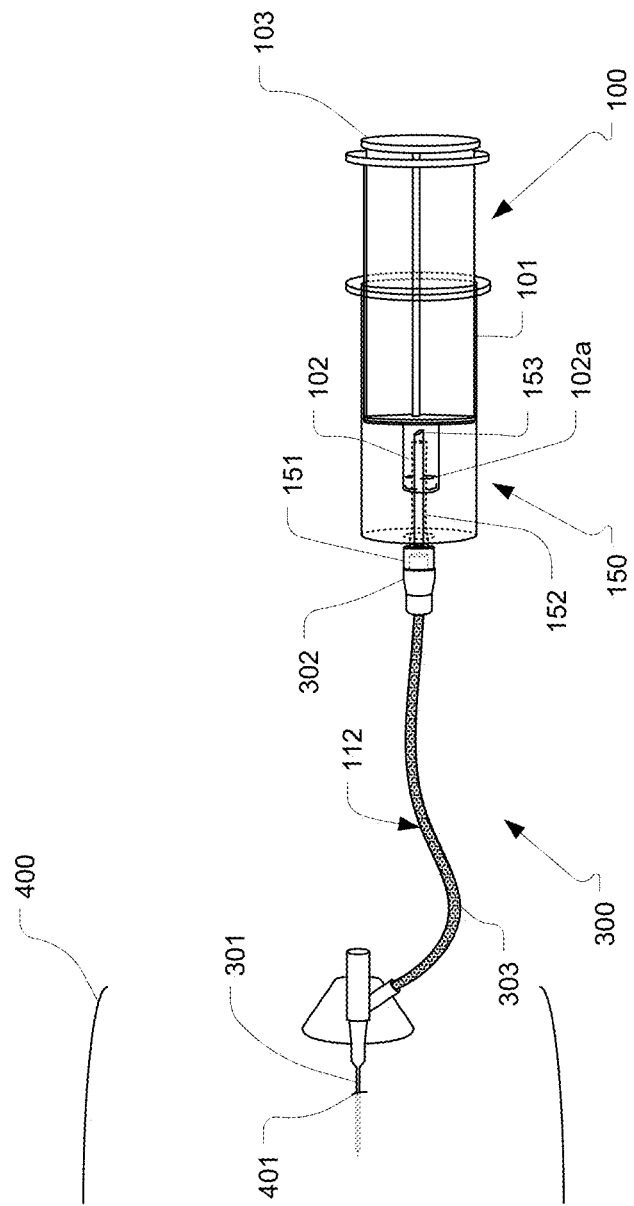
FIG. 4C illustrates that the plunger has been forced towards the adapter thereby injecting fluid into the tube of the PIVC.

FIG. 4C illustrates that plunger 103 has been forced towards adapter 150 thereby injecting fluid 110 into tube 303. Accordingly, tube 303 is shown as containing a mixture 112 of blood 111 and fluid 110.

Figure 4D:
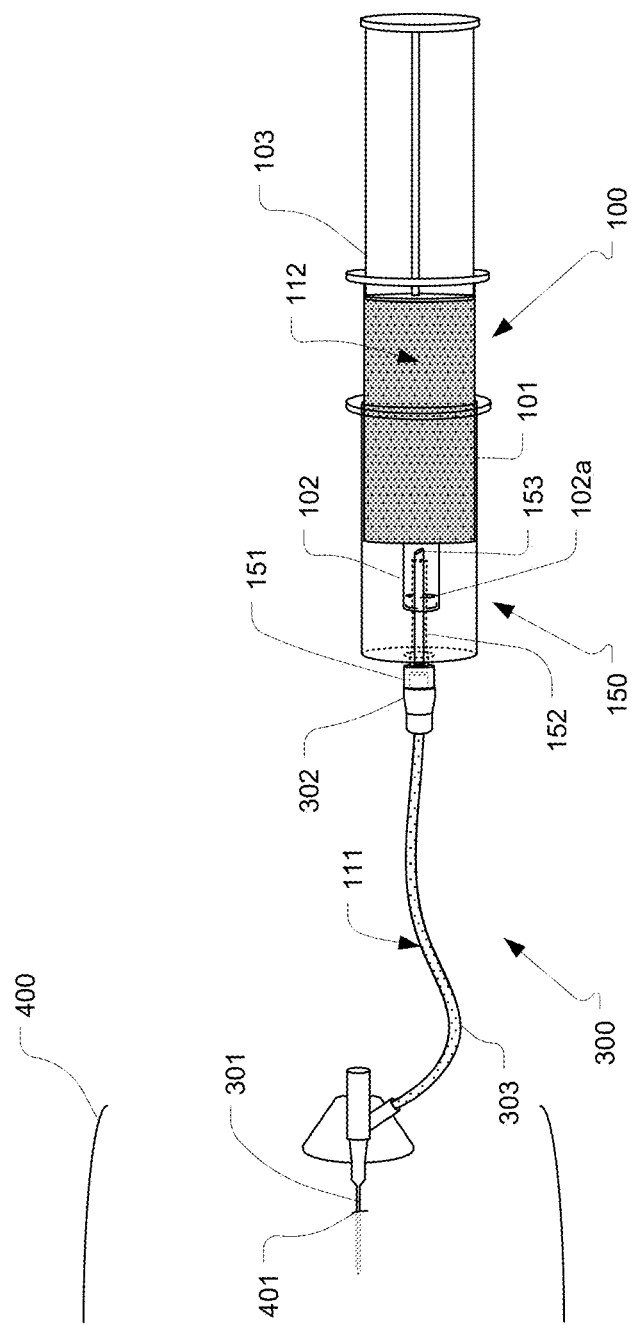
FIG. 4D illustrates that the plunger has been pulled back away from the adapter thereby extracting a mixture into the body of the syringe.

FIG. 4D illustrates that plunger 103 has been pulled back away from adapter 150 thereby extracting mixture 112 into body 101 of syringe 100. Mixture 112 comprises a discard sample of the blood collection process which may be disposed or otherwise used. After the discard sample has been collected, tube 303 again contains blood 111 as shown.

Figure 4E:
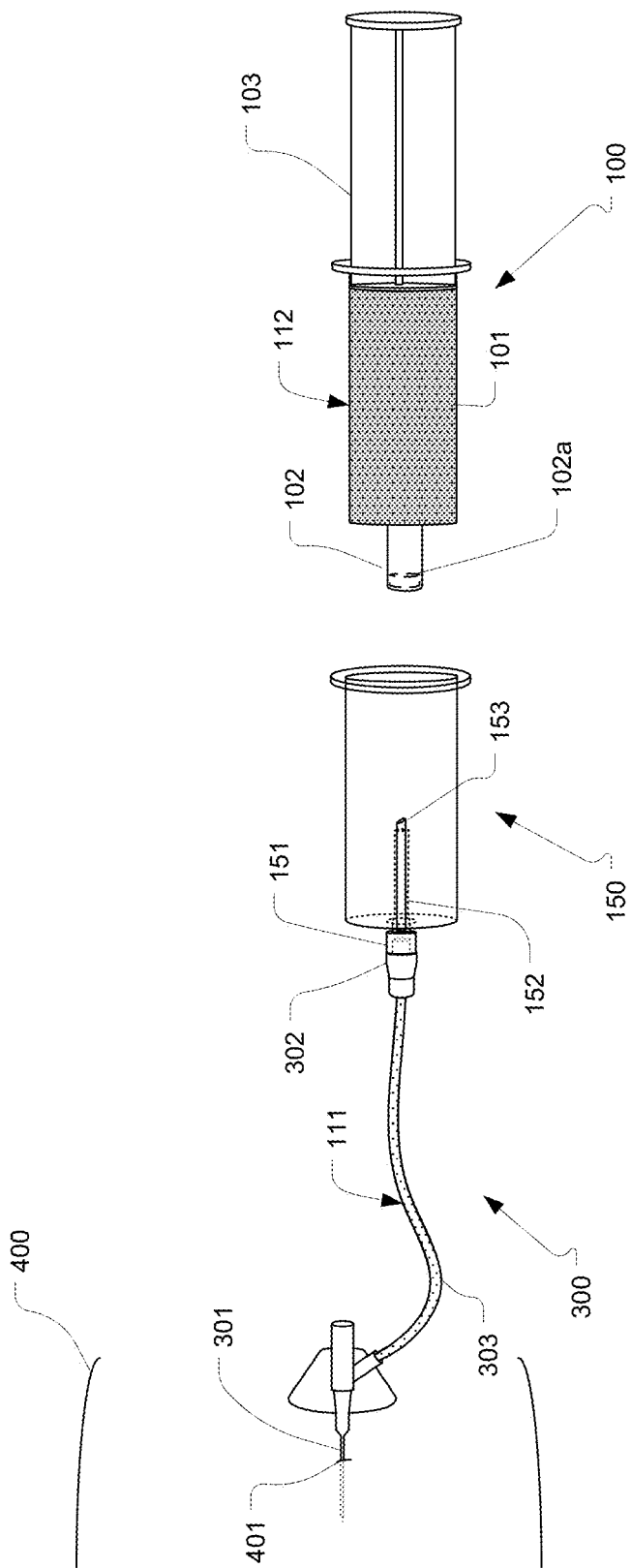
FIG. 4E illustrates that, after the mixture has been extracted from the PIVC, the syringe is detached from the adapter without disconnecting the adapter from the PIVC.

FIG. 4E illustrates that, after mixture 112 has been extracted from PIVC 300, syringe 100 is detached from adapter 150 without disconnecting adapter 150 from PIVC 300. Depending on the interface between syringe 100 and adapter 150, syringe 100 can be removed in various ways. For example, in some embodiments such as when syringe 100 is held within adapter 150 by friction, syringe 100 may be removed by pulling syringe 100 away from adapter 150. In other embodiments, syringe 100 may be held within adapter 150 by some structural interface (e.g. threads, protrusions, indentations, etc.) which may require syringe 100 to be twisted with respect to adapter 150 before syringe 100 can be removed. FIGS. 5 and 6 illustrate on type of structural interface that can be employed between syringe 100 and adapter 150. Other structural interfaces can also be used.

When syringe 100 is removed from adapter 150, cannula 153 remains positioned within the interior of adapter 150 and is ready to receive vacuum-sealed blood tubes or other blood collection devices. Also, adapter 150 remains connected to PIVC 300 (i.e. connectors 151 and 302 remain interconnected). In this way, the closed IV line draw system remains closed during the process of extracting the discard sample and preparing PIVC 300 for blood collection.

Although FIG. 4E shows that sheath 152 remains retracted from the tip of cannula 153, in some embodiments, sheath 152 can be configured to re-cover the tip of cannula 153 once tip 102 of syringe 100 is removed. For example, sheath 152 can be comprised of elastic material (e.g. similar to a material used for septum 102a) which may be biased overtop of cannula 153. In such cases, sheath 152 can provide a seal overtop of cannula 153 so that blood is not allowed to flow out through cannula 153 when syringe 100 is removed. In other cases, a clamp on tube 303 can be used to prevent blood from flowing through cannula 153.

Figure 4F:
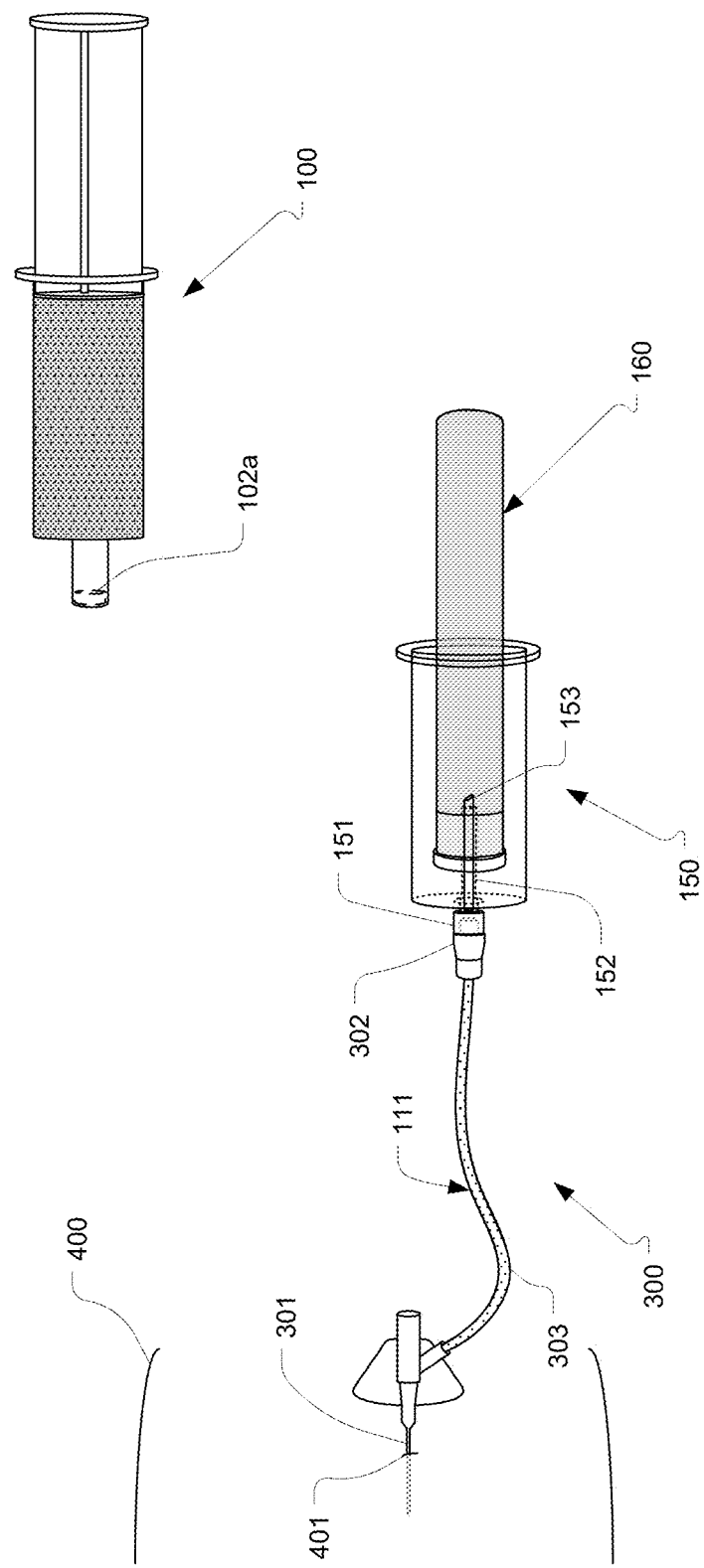
FIG. 4F illustrates that a vacuum-sealed blood tube has been inserted into the adapter to extract blood samples from the PIVC.

FIG. 4F illustrates that a vacuum-sealed blood tube 160 has been inserted into adapter 150 (overtop cannula 153) to extract blood samples from PIVC 300. One or more tubes 160 can be filled in this manner. As can be seen, the system remains closed during the entire blood collection process. In other words, unlike current approaches, no devices are removed from connector 302 of PIVC 300 until after the blood collection process has been completed.

As described above, sheath 152 can be configured to re-cover cannula 153 each time a device (such as tubes 160) is removed from overtop cannula 153. Alternatively, when a sheath is not used or when sheath 152 does not re-cover cannula 153, a clamp or other blocking structure can be used to prevent blood flow through cannula 153 when not desired.

FIGS. 5A, 5B, 6A, and 6B illustrate an example of a securing mechanism for retaining syringe 100 within adapter 150 even while plunger 103 of syringe 100 is pulled outwardly. Because a significant amount of force can be required to pull plunger 103 outwardly, it can be desired to employ some type of structural interface (or securing mechanism) between syringe 100 and adapter 150. For example, a friction only interface may not always adequately secure syringe 100 within adapter 150 while plunger 103 is pulled out. In such cases, a closed IV line draw system that employs some type of structural interface may be desired.

In the example shown in FIGS. 5 and 6, the securing mechanism comprises threads 501 formed on the inside wall of adapter 150 and threads 502 formed on the outside wall of syringe 100. In this way, syringe 100 can be locked within adapter 150, as well as unlocked, by twisting syringe 100 with respect to adapter 150. Threads 501 and 502 can be configured to require a particular amount of rotation between syringe 100 and adapter 150 to enable syringe 100 to be released. For example, the treads can require a quarter, half, three-quarter, or full turn. In some cases, a greater turn may also be required. Accordingly, threads are varying lengths can be used to provide the structural interface.

Other securing mechanisms can also be used to provide a structural interface between syringe 100 and adapter 150. For example, the securing mechanism can comprise a snapping mechanism that engages when syringe 100 is pressed sufficiently into adapter 150. To unlock the snapping mechanism, syringe 100 can be rotated (e.g. a quarter turn) with respect to adapter 150. Alternatively, the snapping mechanism can include one or more narrow channels and corresponding narrow protrusions which must be aligned in order to retract syringe 100.

In some embodiments, as shown in FIGS. 7A-7C, the closed IV line draw system of the present invention can include a POC dispensing adapter 700. FIGS. 7A-7C illustrate how POC dispensing adapter 700 can be integrated into the closed IV line draw system to enable the collection of a POC blood sample during the blood collection process.

As described above, in many scenarios it may be desirable to take a POC sample to provide quick results for certain tests. In many current approaches, the POC test is performed using a separate device from those used to collect larger blood samples. In contrast, the closed IV line draw system of the present invention can be configured to include a POC dispensing adapter that forms an integral component of the system. In this way, the additional functionality of a POC tester can be provided in a singular integrated system.

FIG. 7A illustrates that POC dispensing adapter 700 is connected between connector 151 of adapter 150 and connector 302 of PIVC 300. In some embodiments, the closed IV line draw system can be initially configured with POC dispensing adapter 700 connected to adapter 150. For example, the closed IV line draw system can be packaged and supplied with POC dispensing adapter 700 being connected to connector 151 with syringe 100 also be connected to adapter 150 so that each component is part a singular integral system. In other embodiments, however, POC dispensing adapter 700 can be supplied separately from the other components of the closed IV line draw system. In such cases, POC dispensing adapter 700 can be configured to attach between connector 302 and connector 151 when adapter 150 is connected to PIVC 300.

In either case, as shown in FIG. 7B, POC dispensing adapter 700 remains connected between adapter 150 and PIVC 300 while the discard sample and blood samples are extracted. In this manner, the closed IV line draw system remains closed during the blood collection process even when POC dispensing adapter 700 is used.

FIG. 7C illustrates that, once the blood collection process is completed, POC dispensing adapter 700 can be disconnected from connector 302 and an amount 702 of blood that remains within POC dispensing adapter 700 can be dispensed on POC tester 701 for testing. As shown in FIG. 7C, POC dispensing adapter 700 can remain connected to adapter 150 while dispensing blood 702. Alternatively, POC dispensing adapter 700 can be removed from adapter 150 prior to dispensing blood 702.

In summary, the present invention provides a closed IV line draw system that allows blood samples to be drawn from a PIVC or other type of catheter without requiring multiple connections/disconnections from the catheter. In this way, the blood draw process is simplified and the possibility of contamination to the catheter is reduced. The closed IV line draw system can also minimize the risk of exposure to blood while the technician is drawing the blood samples from the patient.

The closed IV line draw system can be used in other ways than those described above. For example, the closed IV line draw system can be used to flush a vascular access device after which the closed IV line draw system can be removed from the vascular access device. In other words, the closed IV line draw system can be used in a similar manner as described above but without drawing a discard or blood sample. In such cases, the syringe can remain within the adapter while the closed IV line draw system is disconnected from the vascular access device. Alternatively, the empty syringe can be removed from the adapter first and then the adapter can be disconnected from the vascular access device.

Similarly, the closed IV line draw system can be used to draw blood without first flushing the vascular access device. If only blood draw is desired, the syringe can be initially empty (i.e. containing no saline or other solution). Once the adapter is connected to the vascular access device and the syringe inserted over the cannula, a blood sample can be drawn (whether for discard, testing, or another purpose). After the blood is drawn, the syringe can be removed to allow additional blood to be drawn using vacuum tubes or another device, or, if no additional blood is to be drawn, the adapter can be disconnected from the vascular access device while the syringe remains inside the adapter.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of drawing blood, comprising:
connecting an adapter to a vascular access device, wherein the adapter has an open-ended cylindrical shape, wherein the adapter comprises a connector disposed on an exterior of the adapter and a cannula disposed within an interior of the adapter, wherein the cannula extends from the connector;

inserting a syringe within the adapter such that the cannula punctures a septum of the syringe;

in response to the syringe being inserted within the adapter such that the cannula punctures the septum, flushing the vascular access device and collecting a discard sample without removing the syringe from the adapter and without disconnecting the adapter from the vascular access device; and inserting a vacuum-sealed blood tube over the cannula to collect blood from the vascular access device.

2. The method of claim 1, further comprising connecting a point-of-care ("POC") dispensing adapter to the connector of the vascular access device prior to collecting the discard sample and leaving the POC dispensing adapter connected to the connector while the discard sample and blood are collected.

3. The method of claim 2, further comprising dispensing the blood from the POC dispensing adapter while the POC dispensing adapter is connected to the connector of the vascular access device.

4. The method of claim 2, further comprising dispensing the blood from the POC dispensing adapter after disconnecting the POC dispensing adapter from the connector of the vascular access device.

* * * * *